United States Patent [19]

Arai et al.

[11] Patent Number: 5,577,171
[45] Date of Patent: Nov. 19, 1996

[54] FIGURE PATTERN GENERATING APPARATUS FOR DETECTING PATTERN DEFECTS

[75] Inventors: Tooru Arai; Toshiyuki Watanabe; Hideo Tsuchiya, all of Yokohama, Japan

[73] Assignee: Kabushiki Kaisha Toshiba, Kawasaki, Japan

[21] Appl. No.: 25,317

[22] Filed: Mar. 2, 1993

[30] Foreign Application Priority Data

Mar. 2, 1992 [JP] Japan .................................. 4-044209

[51] Int. Cl.$^6$ ............................................... G06K 15/00
[52] U.S. Cl. ........................................... 395/112; 395/101
[58] Field of Search ..................................... 395/112, 101, 395/114, 117, 110; 329/300; 371/25.1

[56] References Cited

U.S. PATENT DOCUMENTS

| | | | |
|---|---|---|---|
| 4,486,745 | 12/1984 | Konno | 340/734 |
| 4,566,002 | 1/1986 | Miura et al. | 340/727 |
| 4,926,489 | 5/1990 | Danielson et al. | 382/8 |
| 5,016,001 | 5/1991 | Minagawa et al. | 340/747 |
| 5,018,210 | 5/1991 | Merryman et al. | 382/8 |
| 5,018,212 | 5/1991 | Manns et al. | 382/8 |
| 5,081,528 | 1/1992 | Hayashi et al. | 358/75 |
| 5,321,354 | 6/1994 | Ooshima et al. | 324/158 |
| 5,335,071 | 8/1994 | Shin | 348/392 |

FOREIGN PATENT DOCUMENTS

| | | |
|---|---|---|
| 58-57726 | 4/1983 | Japan . |
| 58-70532 | 4/1983 | Japan . |

*Primary Examiner*—Raymond J. Bayerl
*Assistant Examiner*—Steven P. Sax
*Attorney, Agent, or Firm*—Oblon, Spivak, McClelland, Maier & Neustadt, P.C.

[57] ABSTRACT

There is provided a pattern generating apparatus in which a figure analyzer analyzes cell data relating to an input figure, figure unfolding sections unfold each basic figure into a figure pattern, the figure unfolding sections are connected in series with pattern memories, the figure unfolding sections and pattern memories are connected in a parallel form to a distribution controller which effects the control operation to cause the figure unfolding sections to effect the unfolding processes for each basic figure unit or each unit obtained by dividing an excessively large figure exceeding a preset threshold value into preset areas, and a readout section having a logical sum circuit for combining partial figure patterns of respective areas from the pattern memories into a single figure pattern outputs the pattern as an output in synchronism with scanning of the input figure.

19 Claims, 10 Drawing Sheets

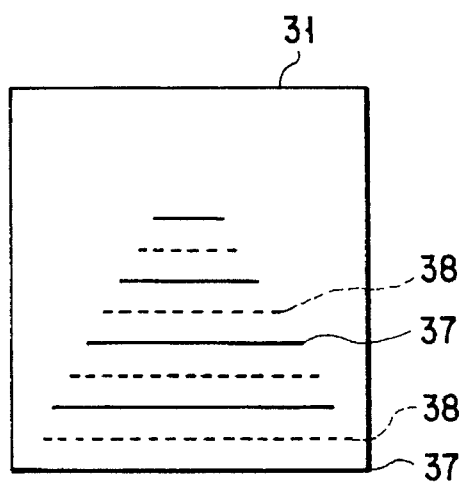
F I G. 6
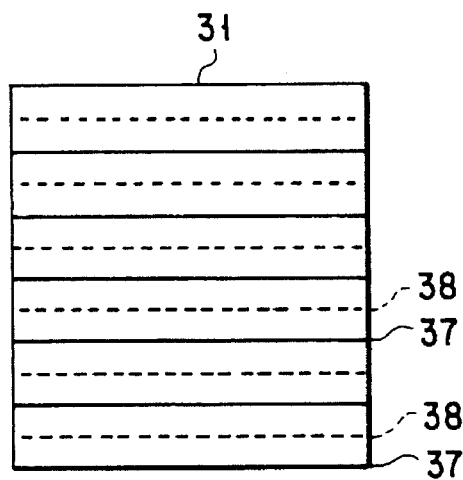
F I G. 7
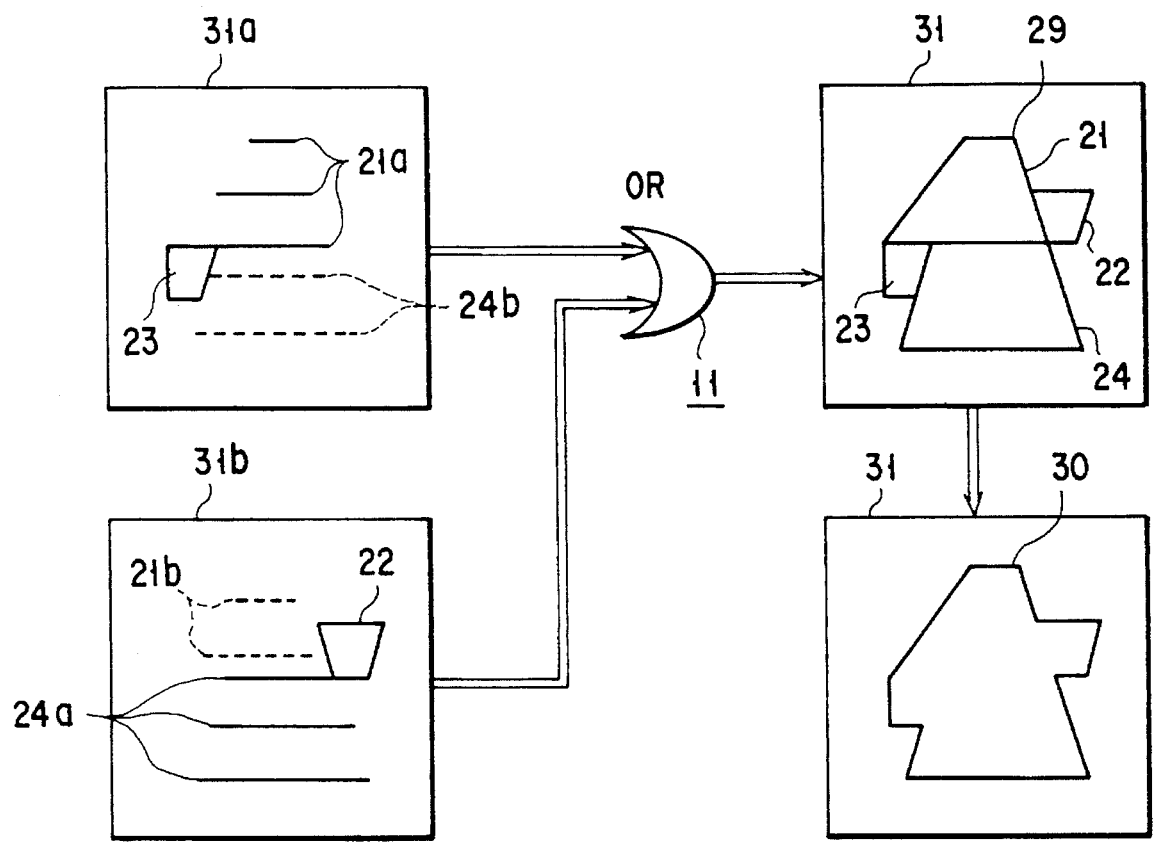
F I G. 8

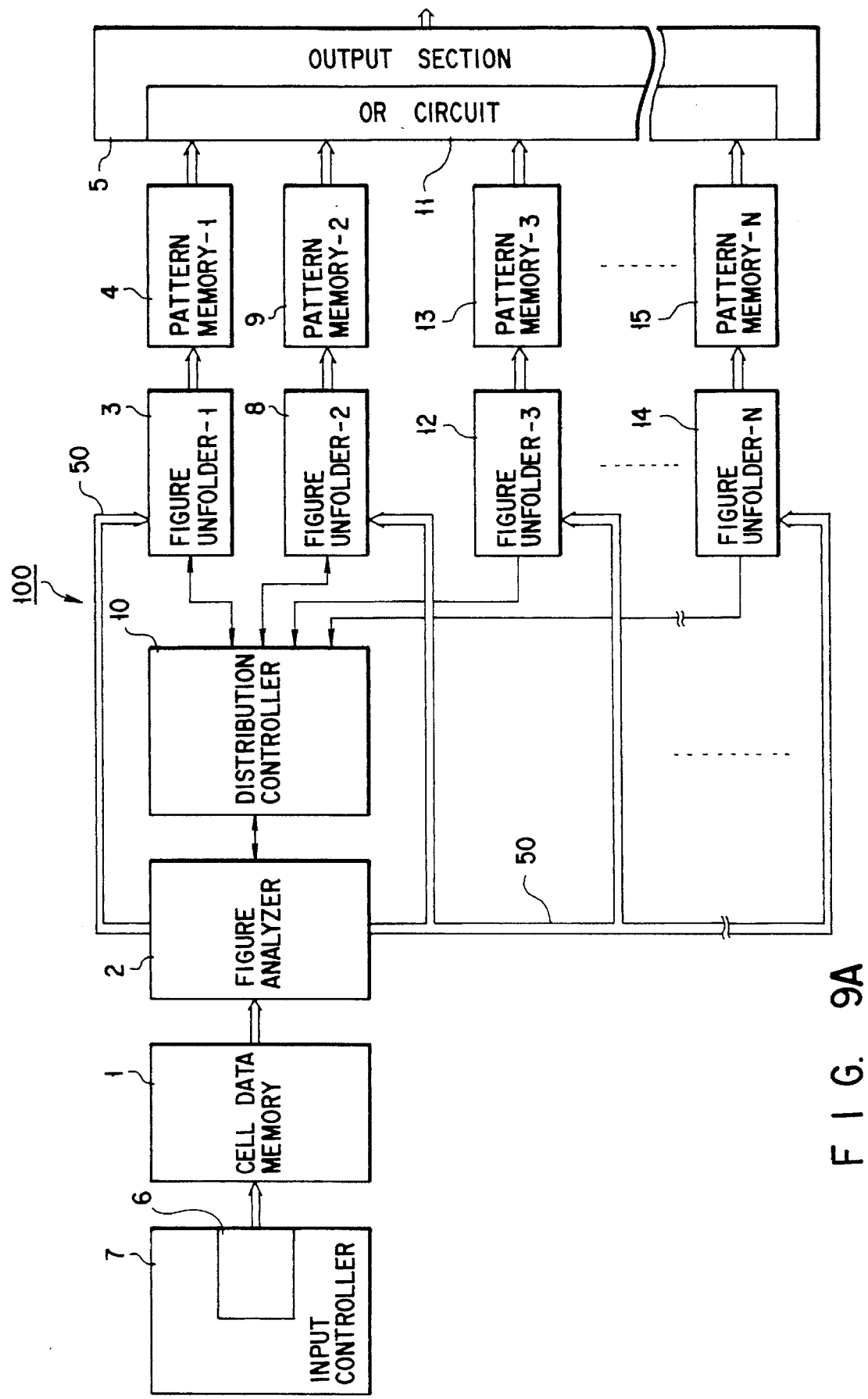
F I G. 9A

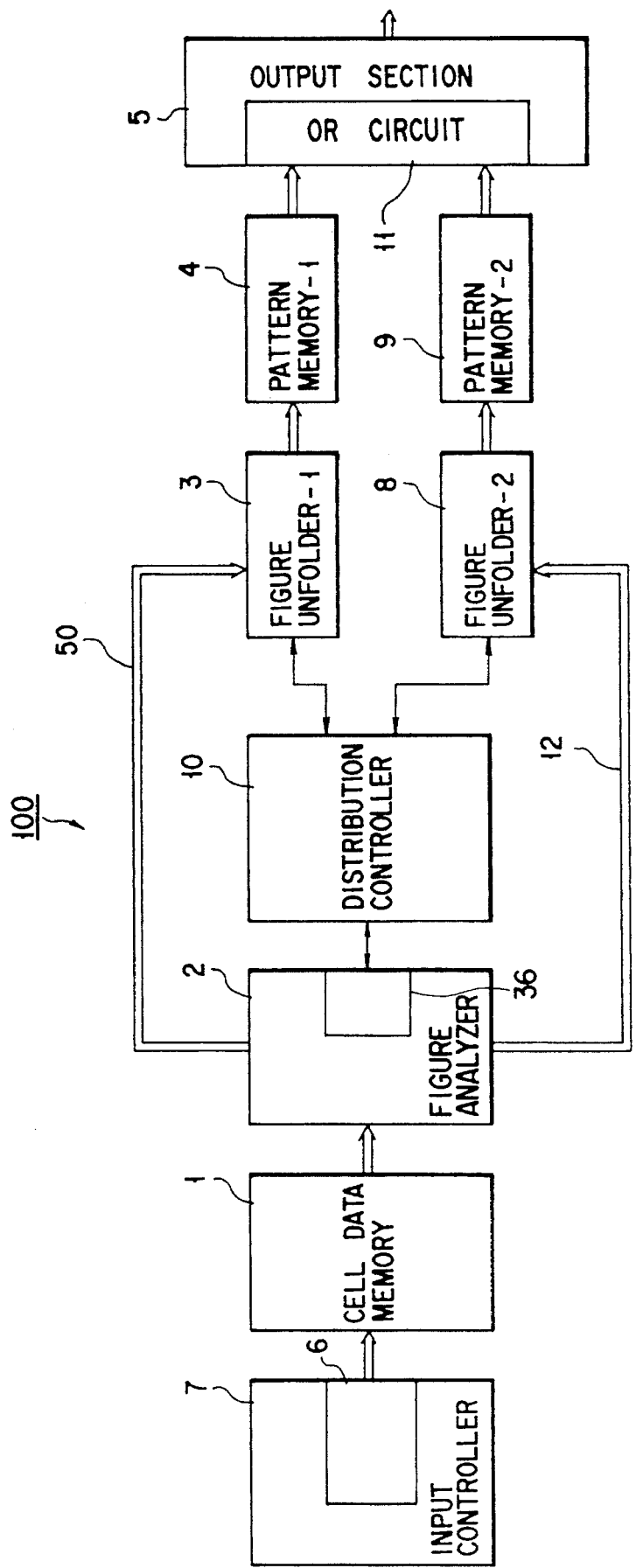
F I G. 9B

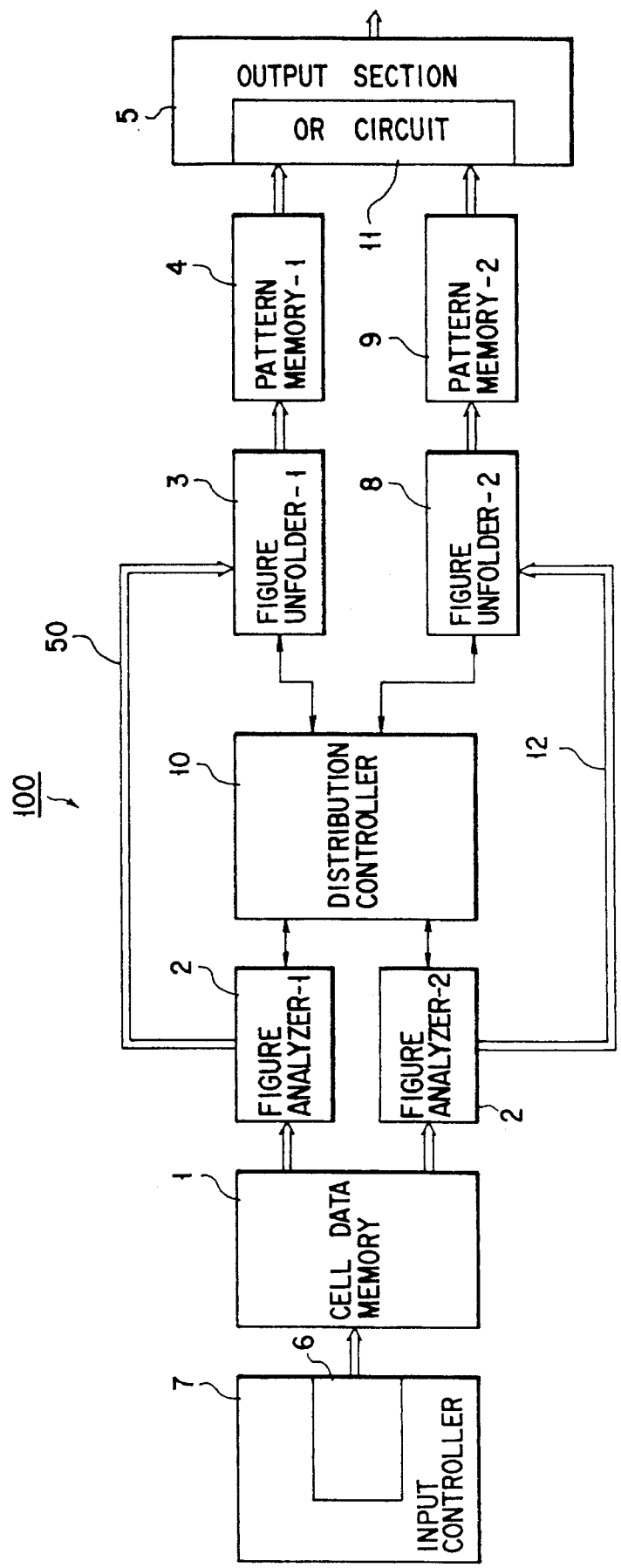
F I G. 9C

FIGURE PATTERN GENERATING APPARATUS FOR DETECTING PATTERN DEFECTS

BACKGROUND OF THE INVENTION

1. Field of the Invention

This invention relates to a pattern generating apparatus utilizing the information processing technique for processing two-dimensional patterns, and more particularly to a pattern generating apparatus such as printer for generating patterns necessary or suitable for generating design data patterns used when pattern defects of reticle patterns and electron beam pattern drawing are inspected in a defect inspection apparatus for reticle patterns used for manufacturing semiconductor integrated circuits and LCDs.

2. Description of the Related Art

As the integration density of the semiconductor integrated circuit is increased, the number of basic figures constructing the pattern of the semiconductor integrated circuit is increased, and as a result, time for drawing the pattern and time for generating patterns used for inspection of the pattern are increased.

The conventional reticle pattern defect inspection apparatus is constructed by elements shown in FIG. 10, for example. A pattern F formed on a photomask 60 is enlarged, the enlarged pattern is divided into strips of a preset width and then the divided portions are continuously scanned. Light passing through the illuminated photomask is made incident on a photodiode array 70 via an enlarging optical system and a pattern is optically formed on the array. The thus formed image is subjected to the photoelectric conversion and then subjected to the A/D conversion by a sensor circuit 80. Measured pattern data output from the sensor circuit 80 is supplied to a comparator 90 together with photomask position data on an XYθ coordinate table output from a positioning circuit. Pattern design data used at the time of formation of the pattern for the photomask 1 is input from a magnetic disk (DK) for storing the data to a bit pattern generator 100 which generates bit (pattern) data and converts the pattern design data to a preset pattern and supplies the pattern to the comparator. The comparator subjects the input bit pattern data to a preset filtering process, compares the thus obtained pattern data with actually measured pattern data and determines that there is a pattern defect when the compared pattern data items do not coincide with each other.

The bit pattern generator 100 is substantially the same as a figure pattern generating apparatus for converting the input image to a bit pattern and generating the bit pattern. The more detailed construction of the conventional pattern generating apparatus corresponding to the above described bit pattern generator 100 is shown in FIG. 11 and the flow of data generated is shown in FIG. 12.

Cell data 112 representing parameters concerning the figure pattern constructed by the basic figures in a compressed form in a microprogramming manner is stored in a third memory 106 of a control section 107. The cell data is transferred from the third memory 106 to a cell data memory 101 which is a first memory at high speed in the unit of cell. After this, the cell data 112 is transferred from the cell data memory 101 to a figure analyzer 102 to convert the cell data 112 represented in a compressed form into coordinate values (i.e. basic figure data 113) for each basic figure.

A figure unfolder 103 receives the basic figure data 113 for each figure, sequentially generates basic figure patterns 114 represented by the basic figure data 113, and transfers the same to a pattern memory 104 which is a second memory. The basic figure pattern 114 generated in the unit of cell is read out from the pattern memory 104 by raster scanning by means of a readout section 105.

In the conventional figure pattern generating apparatus with the above construction, time required for generating the pattern of one cell is generally longer than time for transferring the cell data because of the figure analyzing process and time for figure unfolding becomes longer than time for the figure analysis. This is because the cell data 112 is formed in a microprogramming manner and the figure analysis can be effected by several steps, but each step must be effected for each pixel or every preset number of pixels of the figure in the figure unfolding process. Particularly, when the number of pixels of the figure is large or the number of figures is large, time for the figure unfolding process becomes extremely long.

Therefore, the pattern generation speed of the figure pattern generating apparatus is generally dependent on the unfolding speed of the figure unfolding section 103.

For the reasons described above, in the conventional figure pattern generating apparatus, the operation speed higher than the figure unfolding speed of the figure unfolding section cannot be attained and the pattern generation speed is automatically limited.

SUMMARY OF THE INVENTION

An object of this invention is to provide a pattern generating apparatus capable of reducing time for figure pattern generation for each cell and generating figure patterns at high speed.

In this invention, in order to attain the above object, a pattern generating apparatus comprising a figure unfolding section for dividing a figure pattern to be generated into a plurality of basic figures for each preset area and generating a figure pattern for each basic figure in a preset area according to data representing the basic figure; and a figure combining section for combining the figure patterns generated for each area from the figure unfolding section to generate a desired figure pattern, wherein the figure unfolding section includes a plurality of figure unfolding units which are provided in a parallel form and which processes figures in a corresponding area in a parallel manner.

More specifically, a pattern generating apparatus comprises a cell data memory for storing parameters (which are hereinafter referred to as cell data) of basic patterns which are obtained by dividing a figure pattern to be generated into basic figures for each area defined as a cell of preset size; a figure analyzing section for sequentially reading out cell data from the cell data memory and analyzing the coordinates of each basic figure in each cell area; a figure unfolding section for generating a figure pattern for each basic pattern by use of the analyzed coordinate data; a pattern memory for storing a dot pattern generated by the figure unfolding process for each cell; a readout section for reading out the dot pattern stored in the pattern memory by raster scanning; and a control section for transferring cell data to the cell data memory, the figure unfolding section includes a plurality of figure unfolding units and the pattern memory includes a plurality of pattern memory units and the pattern generating apparatus further comprises a distribution control section connected between the figure analyzing section and the plurality of figure unfolding units and pattern memory units, for sequentially transferring basic figures to those of the figure unfolding units which have finished the figure unfolding process.

Further, in the above distribution control section, there is provided a section for determining the basic figure as a large figure exceeding the threshold value when the size of the basic figure is larger than a preset value (e.g. threshold value), dividing an excessively large figure determination flag and the excessively large figure into a plurality of preset areas when the excessively large figure is received, and sequentially transferring the division number, the excessively large figure determination flag and the same excessively large figure data to those of the figure unfolding units which have finished the unfolding process; the figure unfolding section includes a section for unfolding the figure in an area defined based on the preset condition in the same excessively large figure by the excessively large figure determination flag and the division number, and in the readout section, an output section for combining the figure patterns which are separately unfolded while raster-scanning the same and outputting the combined figure patterns to the plurality of pattern memory units.

With the pattern generating apparatus with the above construction, since a plurality of figure unfolding units provided in parallel can selectively distribute and separately unfold the basic figures (parallel processing) even when the number of basic figures in the cell area is large or when an input to-be-processed object is a large-sized figure which fills a preset cell area, the figure unfolding section can continuously effect the unfolding process (as a whole). Therefore, it becomes possible to provide a pattern generating apparatus which can effect the high-speed process without receiving influence by the limitation of the inherent processing speed of each figure unfolding unit, (thereby making it possible to effectively utilize the operation speed of the computer for controlling this apparatus).

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 6 is a diagram showing the excessively large figure determination process when the figure unfolding section has two parallel figure unfolding units;

FIG. 7 is a diagram showing the excessively large figure determination process when the figure unfolding section has two parallel figure unfolding units;

FIG. 8 is a conceptional diagram for illustrating the pattern unfolding and combining process when the first embodiment is combined with the second embodiment;

FIGS. 9A to 9C are diagrams showing the construction of modifications of the first and second embodiments;

DETAILED DESCRIPTION OF THE PREFERRED EMBODIMENTS (First Embodiment)

A first embodiment of this invention is described with reference to FIGS. 1 to 3.

Figure 1:
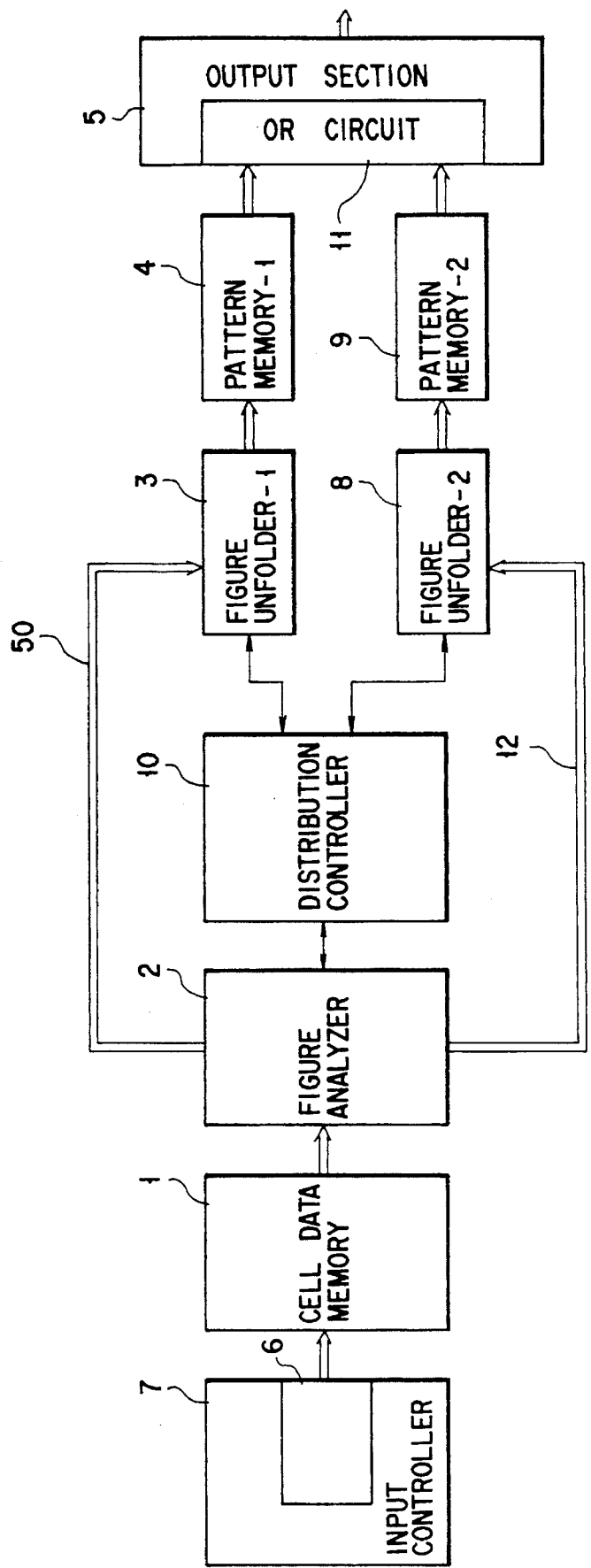
FIG. 1 is a diagram showing the construction of a pattern generating apparatus according to a first embodiment of this invention.

FIG. 1 shows the schematic construction of a pattern generating apparatus according to the first embodiment of this invention.

The common feature of this invention (i.e. the common feature in the first embodiment, second embodiment and the modification) lies in that a plurality of figure unfolding units and a plurality of pattern memories are provided in parallel. In the explanation for the first embodiment, figure unfolding sections 3 and 8 and pattern memories 4 and 9 are arranged in a two-parallel form as shown in the drawing, but it is possible to arrange N (N is a positive integer larger than 2) figure unfolders and N pattern memories in an N-parallel form (the construction will be described later in detail).

A third memory section 6 is provided in a control section 7 for controlling input data, and cell data which is input data is stored in the memory section 6. The cell data is transferred to a cell data memory 1 which is a first memory section under the control of the control section 7. The data transfer control is effected to always fill the cell data memory 1 with data. For example, when one cell data item in the cell data memory 1 is read out from a figure analyzer 2, new cell data is instantly transferred to fill cell data into the cell data memory 1. The data transfer control is continuously effected until cell data is transferred at the maximum speed and all of the cell data to be transferred is read out from the third memory section 6.

The cell data memory 1 may be a stack buffer. Further, the third memory may be an output buffer of a magnetic recording apparatus (DK).

The figure analyzer 2 sequentially reads out cell data from the cell data memory 1, analyzes the cell data for each basic figure in the cell, converts the cell data into coordinate data and transfers the data to a distribution controller 10.

The distribution controller 10 connected to the figure analyzer 2 receives coordinate data (e.g. XYθ coordinate value) of the basic figure for each figure unit and selectively transfers the coordinate data to one of a plurality (two in this example) of figure unfolding sections 3 and 8 connected in parallel which has finished the unfolding process and is set in the standby mode (the selective transfer control will be explained later).

The figure unfolding sections 3 and 8 unfold an input figure according to the received coordinate data and store the results of unfolding process into the pattern memories 4 and 9 which are the second memories.

As described above, the basic figure patterns unfolded and stored in the different pattern memories 4 and 9 are simultaneously read out by a readout section 5 when the unfolding process in the cell area is completed, and then combined into a single pattern figure by a logical sum (OR) circuit 11 provided in the readout section 5 which is an output section of this apparatus.

Figure 2:
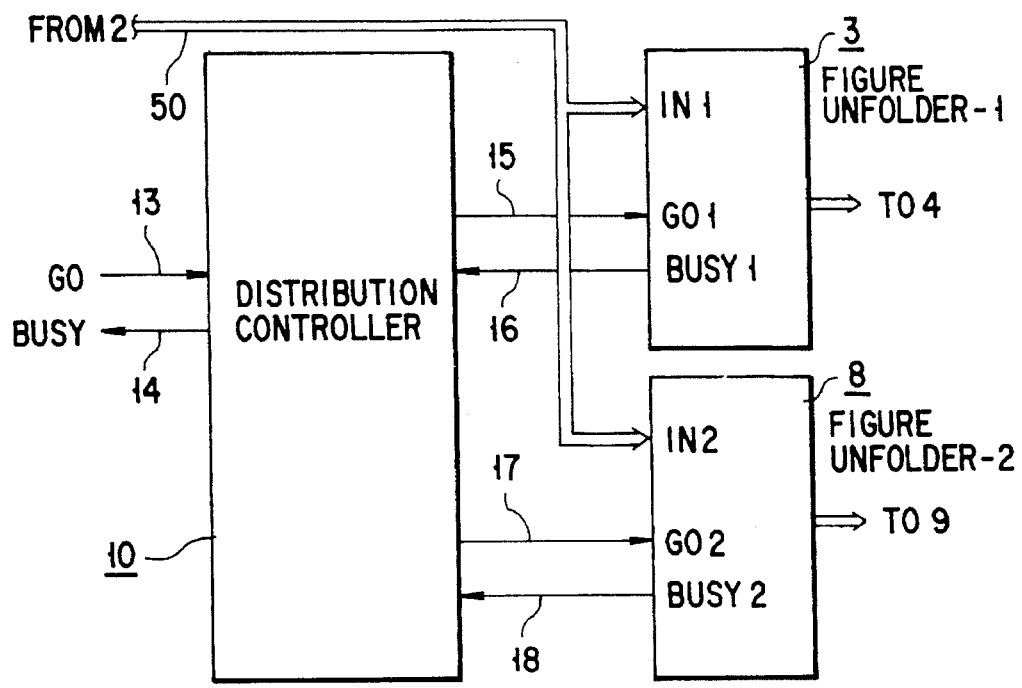
FIG. 2 is a detail diagram for illustrating the operation of a distribution controlling section and a figure unfolding section shown in FIG. 1.

FIG. 2 shows the connection between the distribution controller 10 shown in FIG. 1 and the two figure unfolding sections 3 and 8 and the flow of various control signals and data and shows the distribution control in detail. As shown in FIG. 2, coordinate data transferred for each basic figure from the figure analyzer 2 is transferred via a data bus 50.

when the distribution controller 10 is not in the BUSY state (operating state) 14, coordinate data is prepared from the figure analyzer 2 via the data bus 50 and a GO command (unfolding process starting command) 13 is output. When the distribution controller 10 receives the GO command (unfolding process starting command) 13, it is checked whether or not each of the figure unfolding sections 3 and 8 is set in the BUSY1 state (unfolding operation state) 16 or in the BUSY2 state (unfolding operation state) 18. A GO1 signal (unfolding process starting signal) 15 or GO2 signal (unfolding process starting signal) 17 is supplied to one of the figure unfolding sections 3 and 8 which is not set in the BUSY state (unfolding operation state).

Neither of the figure unfolding sections 3 and 8 is set in the BUSY state (unfolding operation state), the unfolding process starting command GO is output to the figure unfolding section 3 having a higher priority than the other as is previously determined.

On the other hand, when both of the figure unfolding sections 3 and 8 are set in the BUSY state (unfolding operation state), the BUSY state (operating state) signal 14 is output to the figure analyzer 2 via the distribution controller 10 and the standby mode is set until one of the figure unfolding sections 3 and 8 is set into a state which is not the BUSY state (unfolding operation state).

As described above, the distribution control is selectively effected to cause one of the figure unfolding sections 3 and 8 which does not effect the process (which is set in the standby mode) to effect the figure unfolding process, thereby making it possible to permit the figure unfolding section to continuously effect the figure unfolding process as a whole.

Figure 3A:
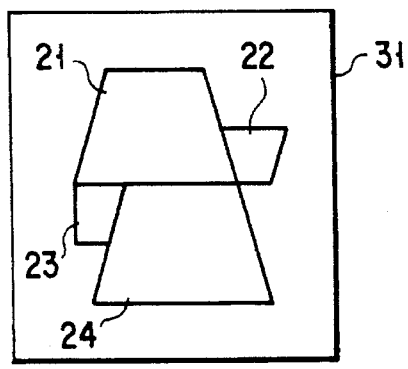
FIGS. 3A to 3C are diagrams showing examples of basic figures unfolded in the pattern generating apparatus of the first embodiment.
Figure 3B:
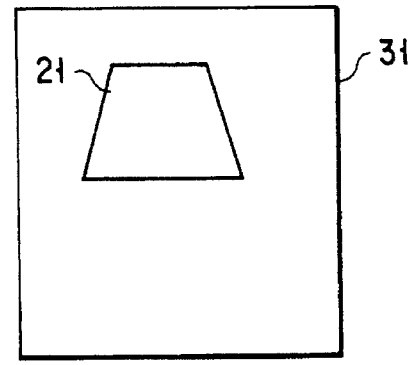
Figure 3C:
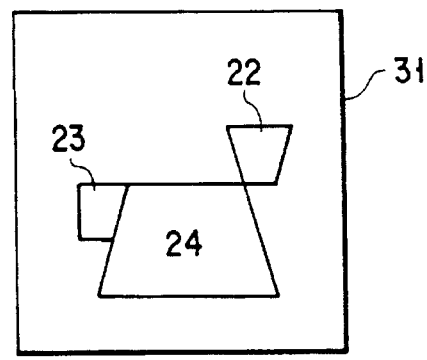

FIGS. 3A to 3C show one example of a figure pattern which is separately processed by a plurality of (e.g. two) figure unfolding sections 3 and 8 by the above-described distribution control after an input figure is divided into a plurality of basic figures (21, 22, 23, 24) in a cell 31 by the pattern generating apparatus of FIG. 1 according to the first embodiment of this invention.

FIG. 3A shows an image of a plurality of basic figure patterns used as the basis of coordinate data input to the distribution controller 10. FIG. 3B shows a figure pattern unfolded by the figure unfolding section 3 and FIG. 3C shows a figure pattern unfolded by the figure unfolding section 8.

In the initial condition of the apparatus, neither of the figure unfolding sections 3 and 8 is set in the BUSY state (i.e. operating state). Therefore, if a higher operation priority (i.e. the highest order) is previously allotted to the figure unfolding section 3, a basic FIG. 21 which is the first object to be processed is first subjected to the unfolding process by the figure unfolding section 3. The unfolding process for a next basic FIG. 22 is started by the figure unfolding section 8. Then, the unfolding process for a next basic FIG. 23 is not started until the unfolding process by one of the figure unfolding sections 3 and 8 is completed, and when the process by one of the figure unfolding sections 3 and 8 is completed, the distribution controller 10 allots the process to that one of the figure unfolding sections 3 and 8 which is now available. In the case of the figure shown in FIGS. 3A to 3C, the basic FIG. 22 has an area smaller than the basic FIG. 21 and the unfolding process for the basic FIG. 22 will be completed earlier than that for the basic FIG. 21 so that it may be determined that the unfolding process for the basic FIG. 23 will be effected by the figure unfolding section 8.

Further, since the total area of the basic FIG. 22 and 23 is smaller than the area of the basic FIG. 21 and the unfolding process for the basic FIG. 23 will be completed earlier than that for the basic FIG. 21 so that it may be determined that the unfolding process for a next basic FIG. 24 will be effected by the figure unfolding section 8.

As described above, a plurality of figure unfolding sections 3 and 8 are used to construct the pattern generating apparatus and the distribution of the unfolding process for each basic figure is controlled by the distribution controller 10 so that a plurality of figure unfolding sections 3 and 8 can continuously effect the unfolding processes for basic figures even when figures with different sizes are input. Therefore, the unfolding processing speed set in a case where a plurality of (i.e. two) sets of the figure unfolding sections and the pattern memories are arranged in parallel is increased to be substantially twice (N times) that of the conventional apparatus constructed by a single figure unfolding section. In general, when N (i.e. integer multiple) sets are arranged in parallel, the processing speed can be enhanced to substantially N times that of the conventional case.

(Second Embodiment)

Next, a second embodiment of this invention is explained in detail with reference to FIGS. 4 to 8.

Figure 4:
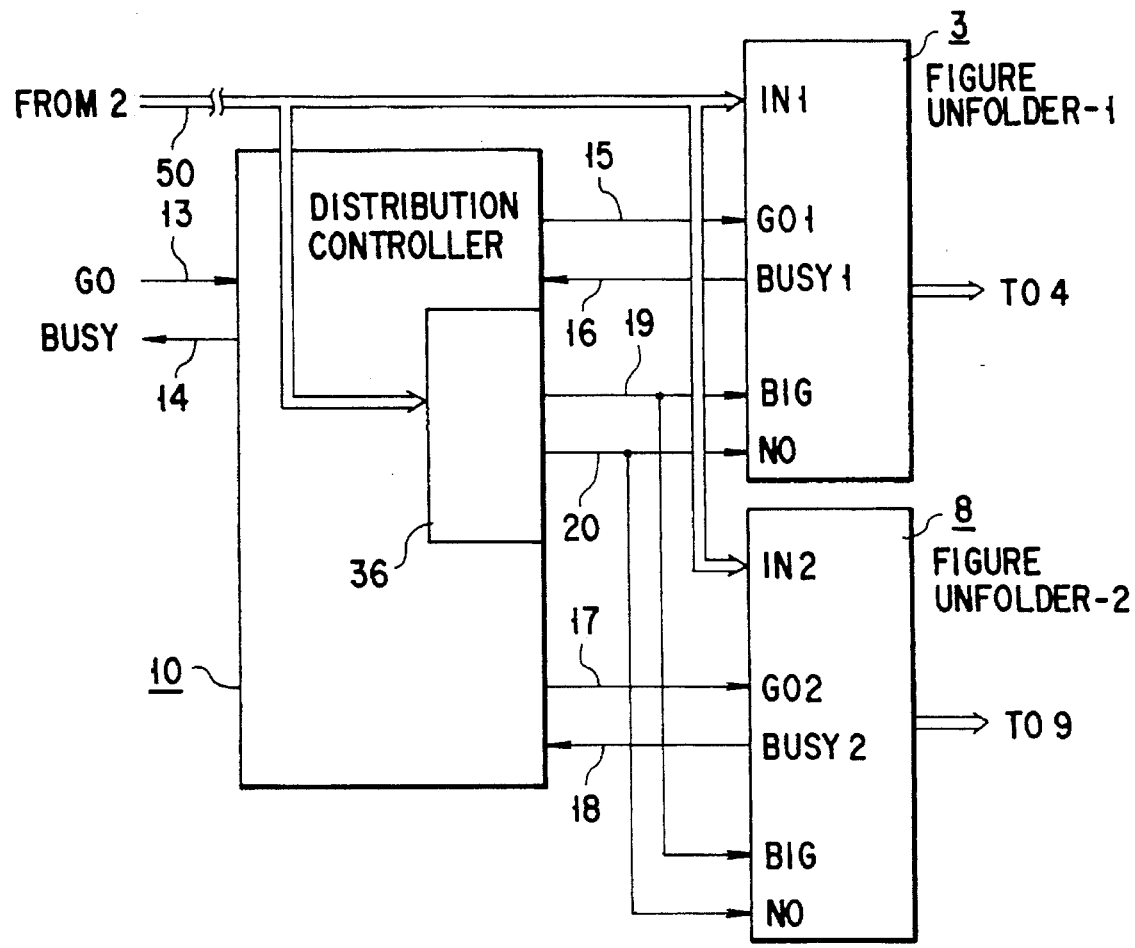
FIG. 4 is a detail diagram for illustrating the operation of a distribution controlling section and a figure unfolding section of a pattern generating apparatus according to a second embodiment of this invention.

FIG. 4 shows the internal construction of the distribution controller 10 shown in FIG. 1 which is the feature of this embodiment, the connection between the two figure unfolding sections 3 and 8, and the flow of data and various signals.

Figures 5A, 5B:
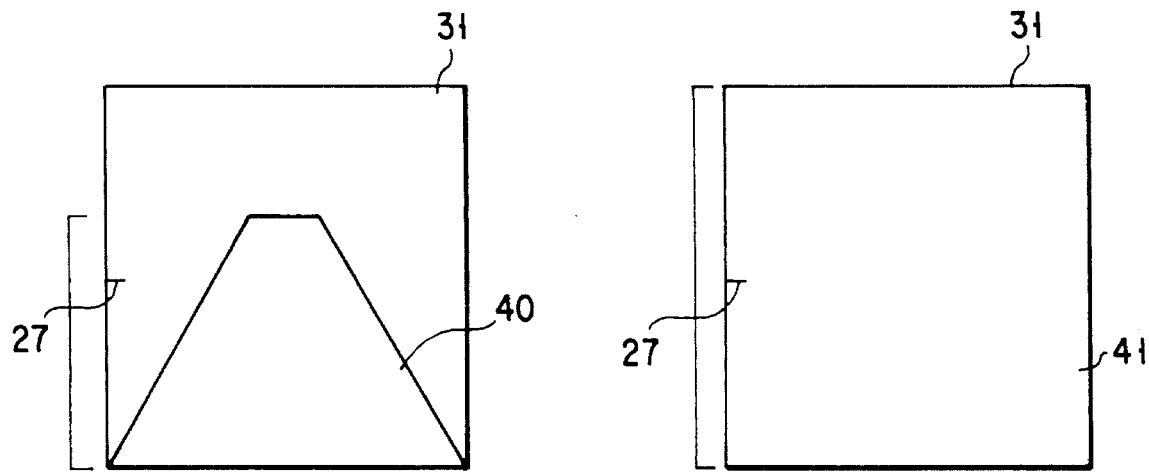
FIGS. 5A and 5B are conceptional diagrams showing the relation between preset values and figures.
Figure 10:
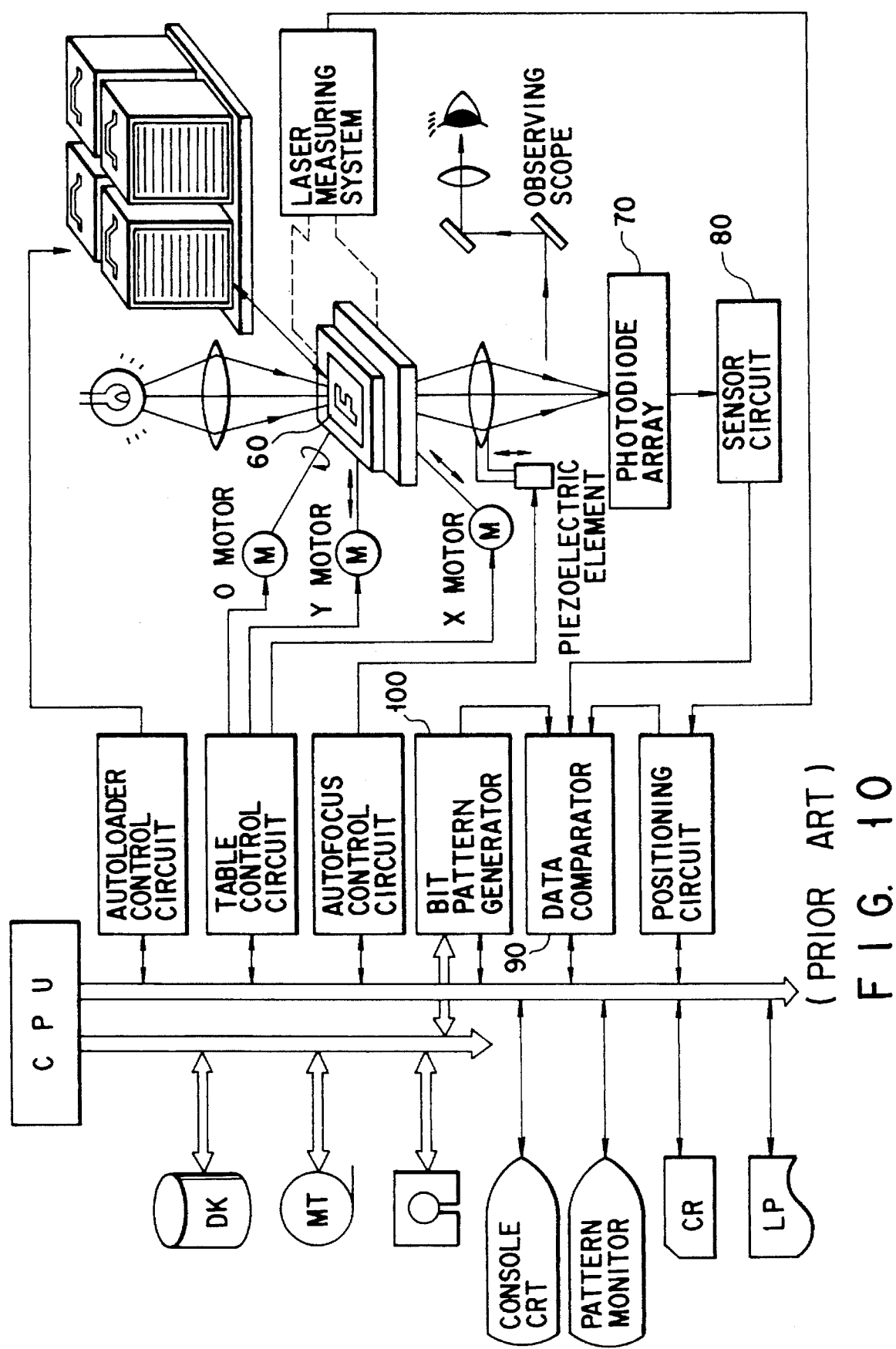
FIG. 10 is a diagram showing the schematic construction of a pattern defect inspection apparatus including the conventional pattern generating apparatus.
Figure 11:
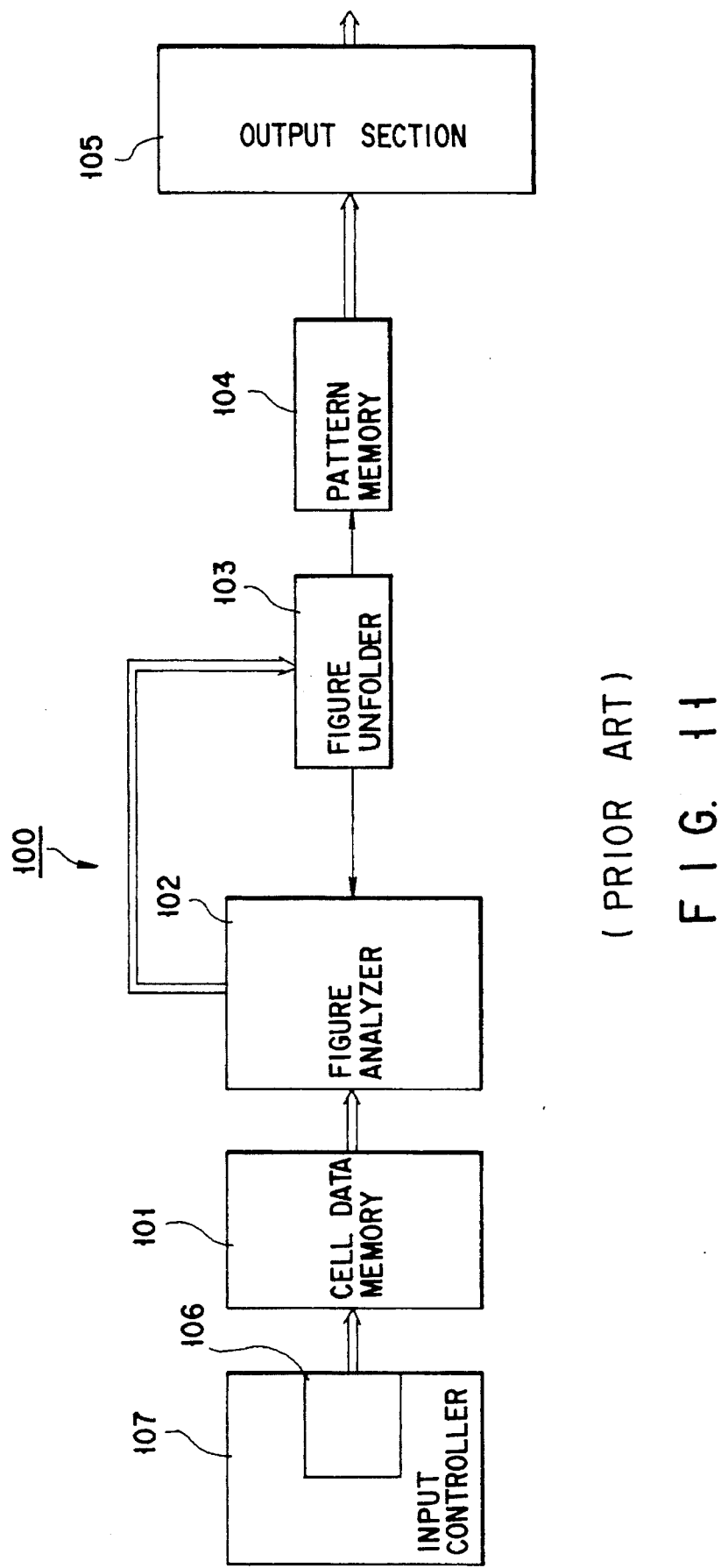
FIG. 11 is a diagram showing the construction of the conventional pattern generating apparatus.
Figure 12:
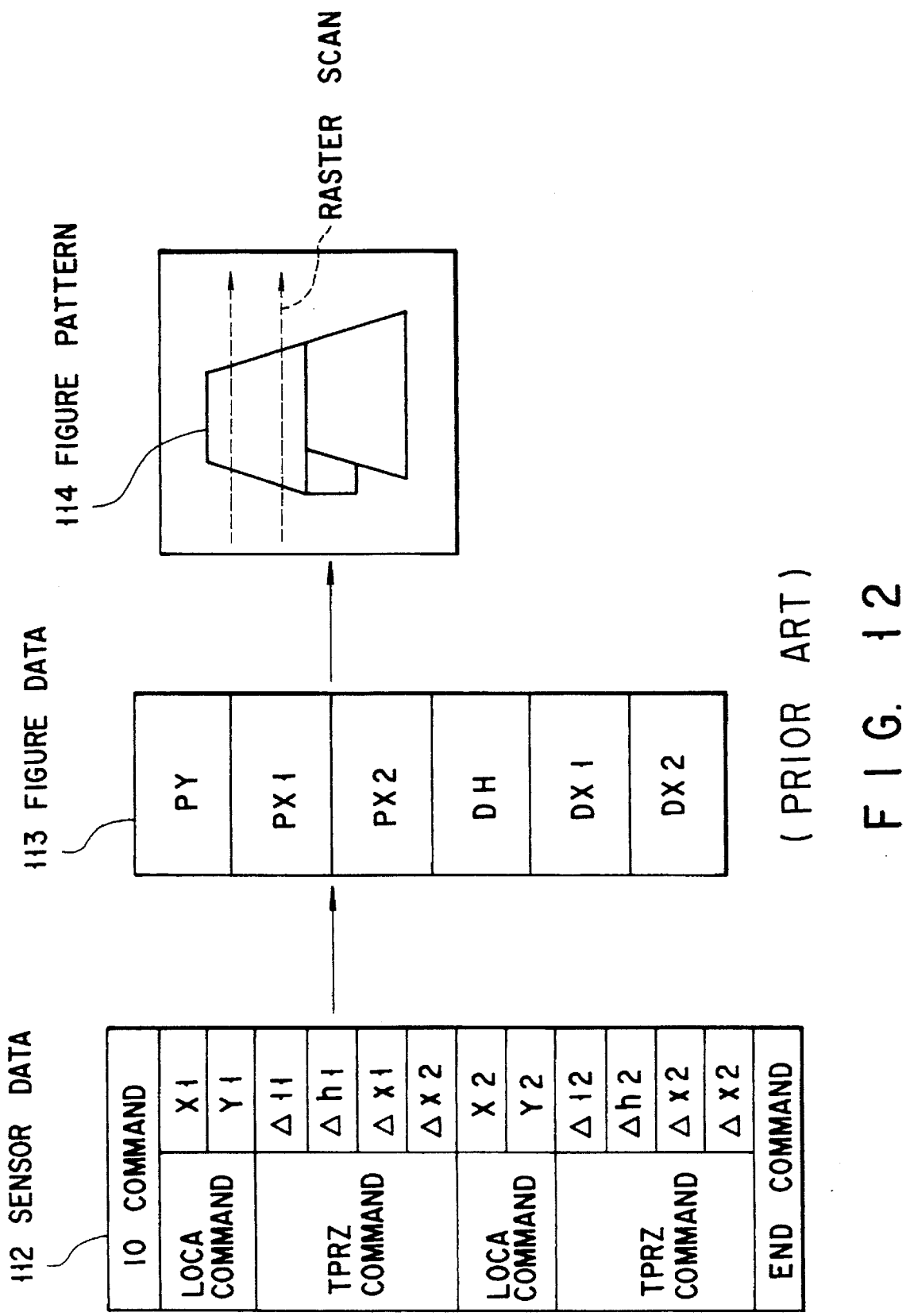
FIG. 12 is a diagram showing the flow of data in the conventional pattern generating apparatus.

FIGS. 5A and 5B are diagrams showing input figures (which are hereinafter referred to as large-sized figures or threshold exceeding figures) which are larger than a preset threshold value. The explanation for portions which are the same as those shown in FIG. 1 is omitted.

The feature of the second embodiment is that an excessively large figure determining section (i.e. excessively large figure determining means) 36 is arranged in the distribution controller 10. The construction of this embodiment permits a series of processes to be efficiently effected according to determination of the size of the figure when a figure (a so-called excessively large figure) larger than a threshold value which is set as the processing condition, for example, a large figure (e.g. trapezoid 40) which fills a large part of the cell 31 as shown in FIG. 5A or a fully occupying FIG. 41 which fully occupies the cell 31 as shown in FIG. 5B is input.

In the distribution controller 10 of FIG. 4, the data bus 50 extending from the figure analyzer 2 (not shown in FIG. 4) is branched into two portions. Like the former embodiment, one of the branch portions is connected to two figure unfolding sections 3 and 8. The other branch portion is connected to the excessively large figure determining section (i.e. excessively large figure determining means) 36 which is provided in the distribution controller 10 and is the feature of this embodiment. The excessively large figure determining section 36 determines whether a figure supplied via the bus 50 is an excessively large figure or not (the determination method will be described later). When it is determined that the input figure is the excessively large figure, an excessively large figure flag 19 for determining that an excessively large figure is input and division number information 20 for individually specifying preset divided areas (which will be described later) are supplied to one of the figure unfolding sections 3 and 8 which is not set in the BUSY state (i.e. operating state) in the same manner as in the first embodiment and coordinate data of the excessively large figure is supplied to one of the figure unfolding sections 3 and 8 which is not set in the BUSY state via the data bus 50.

The assignment information 20 or information indicating whether or not the unfolding process for one basic figure must be assigned to or shared by a plurality of figure unfolding sections and indicating the assignable number which coincides with the number or the numbers (e.g. the number of divisions) of the assignable figure unfolding sections is set to the same number as the number of the figure unfolding sections arranged in parallel. More specifically, in a case where two figure unfolding sections are used as in this embodiment, for example, one example of a method for setting divided areas can be effected by dividing the figure into even-numbered lines and odd-numbered lines of the raster-scanning lines, allotting the unfolding process for the even-numbered lines to the figure unfolding section 3 and allotting the unfolding process for the odd-numbered lines to the figure unfolding section 8. In this case, two numbers corresponding to the even-numbered lines and odd-numbered lines (e.g. the number of divisions is 2) are set in the assignment information.

Like the first embodiment, in the second embodiment, the unfolding process can be substantially continuously effected by use of a plurality of figure unfolding sections 3 and 8, and even when an excessively large figure such as a large-sized figure is input, the process for the excessively large figure can be effected in a short period of time by dividing the large-sized figure into a plurality of areas, allotting the unfolding processes for the divided areas to the respective figure unfolding sections 3 and 8, and simultaneously operating the figure unfolding sections to effect the respective unfolding processes. In comparison with the first embodiment, the unfolding process can be more stably assigned to and effected by a plurality of figure unfolding sections. As a result, when the figure unfolding sections are connected in a two-parallel form as in the first and second embodiments, the unfolding process speed can be enhanced to twice that of the conventional case, and it can be estimated that the unfolding process speed can be enhanced to N times that of the conventional case when N figure unfolding sections are connected in a parallel form (N is a positive integer).

Next, an example of the excessively large figure determination method in the second embodiment and a method for dividing a cell into a plurality of areas and assigning the unfolding processes for the divided areas to a plurality of figure unfolding sections is explained with reference to FIGS. 6 and 7.

FIGS. 6 and 7 show an example of the excessively large figure determination method effected in a case where two figure unfolding sections are provided in a parallel form and FIG. 6 is a schematic diagram showing that the excessively large figure (trapezoid) 40 shown in FIG. 5A is divided into two line groups of even-numbered rows and odd-numbered rows of the raster scanning lines. Further, FIG. 7 is a schematic diagram showing that the excessively large figure (e.g. fully occupying figure) 41 shown in FIG. 5B is divided into two line groups of even-numbered rows and odd-numbered rows of the raster scanning lines.

One example of the excessively large figure determination method is effected by setting a coordinate value 27 which is equal to one half the height of the cell 31 as shown in FIG. 5 as a criterion (i.e. threshold value) and determining an input figure which exceeds the height 27 as an excessively large figure.

The above criterion can be adequately set and it is not limited to one half the height of the cell. The criterion can be set in the form of the width of the figure or the area of the figure. Further, the divided areas can be defined according to lines, memory addresses or the areas of respective portions. The division number of the areas can be set equal to or more than the number of figure unfolding sections provided in parallel.

In the division method of this embodiment, the divided area of odd-numbered lines 37 in the height direction is defined as a division number 1 and the divided area of even-numbered lines 38 is defined as a division number 2.

As described above, after an excessively large figure is determined and divided into a plurality of areas, an excessively large figure flag 19, assignment information 20 and coordinate data corresponding to the excessively large figure are supplied to the distribution controller 10 and to the figure unfolding sections 3 and 8. The figure unfolding sections 3 and 8 receiving the control information and coordinate data subject the areas defined by the assignment information 20 to the unfolding process. For example, in this embodiment, the unfolding process for the odd-numbered lines 37 is assigned to and effected by the figure unfolding section 3 and the unfolding process for the even-numbered lines 38 is assigned to and effected by the figure unfolding section 8.

Partial data items of the large-sized figure assigned to and processed by the figure unfolding sections 3 and 8 as described above are subjected to the logical sum process by an OR circuit 11 in the same manner as in the first embodiment and output as pattern data of a single figure from the output section 5.

The flow of data in the unfolding process effected in a case where the first and second embodiments are combined is schematically shown in FIG. 8. That is, excessively large figures (in this case, the basic FIGS. 21 and 24 are determined as an excessively large figure) and normal figures are provided in a mixed form. In the case of FIG. 8, a cell 31a is a figure pattern which is unfolded by the figure unfolding section 3 and a cell 31b is a figure pattern which is unfolded by the figure unfolding section 8.

The basic FIG. 21 is determined to be an excessively large figure by an excessively large figure determining section 36 (not shown in FIG. 8), the odd-numbered lines 21a thereof are assigned to the figure unfolding section 3 and the even-numbered lines 21b thereof are assigned to the figure unfolding section 8, and the unfolding processes are respectively effected by the figure unfolding sections 3 and 8. However, since the basic FIGS. 22 and 23 which do not exceed the threshold value are not determined to be an excessively large figure, and the unfolding processes for the basic FIGS. 22 and 23 are assigned to the figure unfolding sections 3 and 8 by means of the distribution controller 10 and independently effected by the respective figure unfolding sections 3 and 8. After this, the basic figure 24 is determined to be an excessively large figure by the excessively large figure determining section 36, the unfolding process for the odd-numbered lines 24a thereof is effected by the figure unfolding section 8 and the unfolding process for the even-numbered lines 24b thereof is effected by the figure unfolding section 3.

As described above, a plurality of unfolded figure patterns obtained by selectively effecting the unfolding processes by use of the figure unfolding sections 3 and 8 are combined into a single figure pattern 30 and out-put from the outputting section 5 by reading out data items in the same positions on the respective cell areas via the logical sum (OR) circuit 11 to reproduce the input basic FIG. 29.

(Modification-1)

This invention is not limited to the above embodiments and can be variously modified without departing from the technical scope thereof.

The example shown in FIG. 9A is a modification of the first and second embodiments. That is, this example is made by improving the construction of the apparatus shown in FIG. 1 and N figure unfolding sections (3, 8, 12, - - - , 14) and N pattern memories (4, 9, 13, - - - , 15) are arranged in a parallel form. Pattern data items processed by the respective parallel processings are combined into a single figure pattern by means of the logical sum circuit 11 in the same manner as in the above-described manner and output from the outputting section 5. The operations of the respective constituents are the same as those explained in the first and second embodiments. The main feature of this modification is that the figure unfolding process is effected by use of a parallel construction having elements of N (which may be set to 10 to 30, for example) which is relatively larger than 2. With this construction, the processing speed can be significantly enhanced, and as the integration density of the integrated circuit is increased, this apparatus can deal with more complicated and larger figures. Further, the reliability of the process can be enhanced.

(Modification-2)

The excessively large figure determining section 36, which characterizes the second embodiment shows in FIG. 4, may be incorporated in the figure analyzer 2 as is shown in FIG. 9B.

(Modification-3)

Whether the figure is excessively large or not may be determined by the cell data memory 1 or an device connected to the pattern generating apparatus 100. Alternatively, the excessively large figure determining section 36 may be connected between the cell data memory 1 and the figure analyzer 2, in order to determine whether the figure is excessively large or not. In each of these cases, any data representing an excessively large figure can be stored in two alternative methods. The first method is to store the data, along with a flag indicating that the data represents an excessively large figure. The second method is to divide the data into a small clusters, each representing a part of the figure having a size equal to or smaller than a predetermined one, and to store these clusters of data.

(Modification-4)

Two or more figure analyzers 2 may be connected to the input of the distribution controller 10, rather than only one figure analyzer. More specifically, as is shown in FIG. 9C, two figure analyzers 2 may be connected to the distribution controller 10.

According to the present invention, the arrangement of the figure-analyzing section, the distribution-controlling section, and the pattern-unfolding section in various ways other than those described above.

(Effect of this Invention)

As described above, according to the pattern generating apparatus of this invention, since a figure pattern created by a complicated combination of basic figures in the cell can be generated by use of the parallel construction of N figure unfolding sections and N pattern memories by efficiently assigning the unfolding processes to the figure unfolding sections so as to reduce the time in which at least one of the figure unfolding sections is set in the standby mode irrespective of the condition of an input figure (for example, the shape, size and complicatedness), a pattern generating apparatus in which the operation speed, efficiency and reliability of the figure unfolding process itself can be enhanced can be provided. As the integration density of the integrated circuit is increased, more complicated and larger figures can be dealt with.

Further, as the second effect, a pattern defect inspection apparatus including a pattern generating apparatus which can be contribute to the high efficiency by an increase in the operation speed of the inspection process by the parallel processing can be obtained.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A figure pattern generating apparatus having a predetermined input and output and controlled by a central controller for monitoring and controlling the input and output of a pattern defect inspection apparatus including the central controller, comprising:

figure analyzer for analyzing unit figure information represented by input basic figures corresponding to typical geographical figures in a predetermined form;

a plurality of figure unfolders for unfolding each of the basic figures supplied from said figure analyzer into a plurality of figure patterns;

distribution controller connected to said plurality of figure unfolders in a parallel form, for effecting the distribution control process to assign unfolding process for a basic figure unit or a divided unit obtained by dividing an excessively large figure which exceeds a preset threshold value into predetermined areas to said plurality of figure unfolders; and figure combiner for combining pattern information items which have been subjected to the unfolding process into a single figure pattern.

2. The pattern generating apparatus according to claim 1, further comprising excessively large figure determiner for determining the basic figure as an excessively large figure when the basic figure is larger than a predetermined threshold value, dividing the excessively large figure into a plurality of areas according to a predetermined dividing condition, and allotting said intermediate data in the divided area to said plurality of figure unfolders according to a preset distribution condition to form a figure pattern.

3. The pattern generating apparatus according to claim 2, wherein said distribution condition is a condition for selectively allotting the process and monitoring the operating conditions of said figure unfolders so as to cause the unfolding process to be preferentially assigned to one of said figure unfolders which is set in the standby mode or in the nonoperating state, and said dividing condition is a condition for causing the unfolding process for one excessively large figure to be separately assigned to said plurality of figure unfolders and the unfolding process for the divided area is selectively effected by one of said figure unfolders according to different directions in which the excessively large figure is scanned.

4. The pattern generating apparatus according to claim 2, wherein said threshold value is area or length of a predetermined portion of the basic figure.

5. The pattern generating apparatus according to claim 1, further comprising distribution controllers for selectively allotting the unfolding process to said plurality of figure unfolders based on a preset condition and causing said figure unfolders to effect the unfolding process for forming the pattern of the basic figure, said preset condition is a distribution condition for selectively allotting the process and monitoring the operating conditions of said figure unfolding means so as to cause the unfolding process to be preferentially assigned to one of said figure unfolders which is set in standby state or in non-operating state.

6. The pattern generating apparatus according to claim 1, which further comprising first memory for temporarily storing the unit figure information for each unit of a preset size; and second memory for respectively temporarily storing information items representing patterns of basic figures supplied from said plurality of figure unfolders;

wherein said plurality of figure unfolders means and a plurality of said second memory are combined and each of said second memory are connected in a parallel form to said figure combiner.

7. The pattern generating apparatus according to claim 6, wherein said figure combiner connected to a plurality of said second pattern memories in a parallel form, for combining patterns from said second memory into a single pattern by deriving the logical sum thereof.

8. The pattern generating apparatus according to claim 1, wherein said figure combiner includes a logical sum circuit connected to a plurality of said pattern memory means in a parallel form, for combining patterns from said second memory into a single pattern by deriving the logical sum thereof.

9. A pattern generating apparatus having a predetermined input and predetermined output and controlled by a central controller for monitoring and controlling the input and output, comprising:

figure analyzer for analyzing input cell data formed by representing information relating to the pattern of a figure represented by input basic figures in a preset form;

figure unfolder for unfolding each of the basic figures supplied from said figure analyzer into a plurality of figure patterns;

first memory for temporarily storing the cell data for each cell unit of a preset size;

second memory for respectively storing basic figure pattern data supplied from said figure unfolder;

wherein said plurality of figure unfolder and said plurality of second memories being respectively formed of a combination of a plurality of figure unfolders and a combination of a plurality of second memories which are arranged and operated timely in parallel;

and further comprising:

distribution controller for effecting the predetermined distribution control process to assign the unfolding process for a basic figure unit or a divided unit obtained by dividing an excessively large figure which exceeds a predetermined threshold value into predetermined areas to said figure unfolder;

wherein said distribution controller being connected to said figure analyzer and said plurality of figure unfolders, monitoring the operating conditions of said figure unfolders, causing one of said figure unfolders which is set in standby state or in non-operating state to start the unfolding process and storing pattern data created at the time of completion of the process into said second memory; and a readout section having figure combiner connected to said plurality of second memories in a parallel form, for combining pattern data items into a figure pattern.

10. The pattern generating apparatus according to claim 9, wherein said figure combiner includes a logical sum circuit connected to a plurality of said pattern memories in a parallel form, for combining patterns from said second memory into a single pattern by deriving the logical sum thereof.

11. The pattern generating apparatus according to claim 9, wherein said threshold value is area or length of a predetermined portion of the basic figure.

12. A figure pattern generating apparatus of pattern inspection apparatus having means for comparing a pattern of a testing object with a predetermined reference pattern data, comprising:

figure analyzer for analyzing input cell data formed by representing information relating to the pattern of a figure represented by input basic figures in a predetermined form;

a plurality of figure unfolders for dividing input data of a predetermined size into a plurality of basic figures for each area and generating a figure pattern for each basic figure in predetermined area according to intermediate data representing said basic figure;

distribution controller for selectively allotting the unfolding process performed by said figure unloaders based on a predetermined condition and causing said figure unfolders to effect the unfolding process for forming the pattern of the basic figure; and figure combiner connected to a plurality of said figure unfolders in a parallel form, for combining a plurality of figure patterns for each area which are subjected to unfolding process performed by said figure unfolders to form a desired figure pattern.

13. The pattern generating apparatus according to claim 12, further comprising:

distribution controller for selectively allotting a unfolding process to said plurality of figure unfolders based on a predetermined condition and causing said figure unfolders to effect the unfolding process for forming the pattern of said basic figure, wherein said predetermined condition is a distribution condition for selectively allotting the process and monitoring operational conditions of said figure unfolders so as to cause the unfolding process to be preferentially assigned to one of said figure unfolders which is set in standby state or in non-operating state.

14. The pattern generating apparatus according to claim 12, further comprising:

excessively large figure determiner for determining said basic figure as an excessively large figure when said basic figure is larger than a predetermined threshold value, dividing the excessively large figure into a plurality of areas according to a predetermined dividing condition, and allotting said intermediate data in the divided area to said figure unfolders according to a predetermined distribution condition to form a figure pattern.

15. A pattern generating apparatus according to claim 14, wherein said distribution condition is a condition for selectively allotting the process and monitoring operational conditions of said figure unfolders so as to cause unfolding process to be preferentially assigned to one of said figure unfolders which is set in standby state or in non-operating state, and said dividing condition is a condition for causing the unfolding process for one excessively large figure to be separately assigned to said plurality of figure unfolders and the unfolding process for the divided area is selectively effected by one of said figure unfolders according to different directions in which the excessively large figure is scanned.

16. The pattern generating apparatus according to claim 14, wherein said threshold value is area or length of a predetermined portion of the basic figure.

17. A pattern generating apparatus associated with a figure pattern inspection apparatus used for manufacturing semiconductor devices, comprising:

a plurality of figure unfolders for dividing input data of a predetermined size into a plurality of basic figures for each area and generating a figure pattern for each basic figure in the area according to intermediate data representing said basic figure;

figure combiner connected to said plurality of figure unfolders in a parallel form, for combining a plurality of figure patterns for each area which are subjected to a unfolding process performed by said figure unfolders to form a desired figure pattern;

distribution controller for allotting the unfolding process to said plurality of figure unfolders based on a predetermined condition and causing said figure unfolders to effect the unfolding process for forming the pattern of said basic figure; and excessively large figure determiner for determining said basic figure as an excessively large figure when said basic figure is larger than a predetermined threshold value, dividing the excessively large figure into a plurality of areas according to a predetermined dividing condition, and allotting the intermediate data in the divided area to said plurality of figure unfolders according to a predetermined distribution condition to form a figure pattern.

18. The pattern generating apparatus according to claim 17, wherein said distribution condition is a condition for selectively allotting the process and monitoring the operational conditions of said figure unfolders so as to cause the unfolding process to be preferentially assigned to one of said figure unfolders which is set in standby state or in nonoperating state, and said dividing condition is a condition for dividing the excessively large figure into a plurality of areas when the basic figure is determined to be an excessively large figure.

19. A pattern generating apparatus comprising:

figure analyzer for at least two figure unfolders for analyzing figure information represented by input basic figures as unit figure information represented in a preset form;

at least two figure unfolders for unfolding each basic figure supplied from said analyzer into a plurality of figure patterns;

at least two memories connected in one-to-one correspondence to said figure unfolding means, for temporarily storing unfolded pattern information;

distribution controller connected to said plurality of figure unfolders in a parallel form, for effecting the preset distribution control process to assign the unfolding process for a basic figure unit or a divided unit obtained by dividing an excessively large figure which exceeds a determined threshold value into predetermined areas to said figure unfolders; and figure combiner for combining pattern information items from said memory into a single figure pattern.

* * * * *